United States Patent [19]

Pennella

[11] 4,320,071

[45] Mar. 16, 1982

[54] CONVERSION OF OLEFINIC NITRILES

[75] Inventor: Filippo Pennella, Bartlesville, Okla.

[73] Assignee: Phillips Petroleum Company, Bartlesville, Okla.

[21] Appl. No.: 713,075

[22] Filed: Aug. 9, 1976

Related U.S. Application Data

[63] Continuation of Ser. No. 751,741, Aug. 12, 1968, abandoned.

[51] Int. Cl.$^3$ ............... C07C 120/00; C07C 121/30; C07C 121/48; C07C 121/70
[52] U.S. Cl. ............... 260/464; 260/465 K; 260/465.9
[58] Field of Search ............ 260/464, 465.9, 465 K

[56] References Cited

U.S. PATENT DOCUMENTS

| | | | |
|---|---|---|---|
| 2,384,630 | 9/1945 | Mahan | 260/465.9 |
| 2,451,386 | 10/1948 | Hager | 260/465.8 R |
| 2,478,258 | 8/1949 | Harlow | 260/465.8 R |
| 2,478,285 | 8/1949 | Langkammerer | 260/465.8 R |
| 3,141,034 | 7/1964 | Krebaum | 260/465.9 |
| 3,261,879 | 7/1966 | Banks | 260/683 R |
| 3,365,513 | 1/1968 | Heckelsberg | 260/683 R |
| 3,437,698 | 4/1969 | O'Grady et al. | 260/615 A |
| 3,974,196 | 8/1976 | Nakamura et al. | 260/465.9 |
| 4,088,672 | 5/1978 | Waddan | 260/465.8 R |
| 4,217,299 | 8/1980 | Nakamura et al. | 260/465.8 R |

FOREIGN PATENT DOCUMENTS 1285431  8/1972  United Kingdom ......... 260/465.8 R

OTHER PUBLICATIONS

Foster, C.A., 75(1971) p. 63172b.

Primary Examiner—Joseph Paul Brust

[57] ABSTRACT

One or more olefinically unsaturated nitriles are converted to other nitriles by contact with a catalyst active for the disproportionation of propylene to ethylene and butene.

14 Claims, No Drawings

CONVERSION OF OLEFINIC NITRILES

This application is a continuation of application Ser. No. 751,741, filed Aug. 12, 1968, now abandoned.

This invention relates to the conversion of olefinically unsaturated nitriles by the nitrile reaction.

In many instances it is desirable to convert olefinically unsaturated nitrile compounds into other olefinically unsaturated compounds which may have more economic value at a particular time and location.

An object of the invention is to convert olefinically unsaturated nitrile compounds into other olefinically unsaturated compounds.

According to the invention olefinically unsaturated nitriles are converted into other olefinically unsaturated compounds using solid catalysts active for converting propylene to ethylene and butene by disproportionation.

The term "nitrile reaction" as used herein is defined as a process for the catalytic conversion over a catalyst of a feed comprising one or more olefinically unsaturated nitrile compounds to produce a resulting product which contains at least 10 percent by weight of product compounds, which product compounds can be visualized as resulting from at least one primary reaction, as defined below, or the combination of at least one primary reaction and at least one unsaturated bond isomerization reaction, and wherein the sum of the compounds contained in said resulting product consisting of hydrogen, saturated compounds, and compounds which can be visualized as formed by skeletal isomerization but which cannot be visualized as formed by one or more of the above-noted reactions, comprises less than 25 percent by weight of the total of said resulting product. Feed components and unsaturated bond isomers thereof are not included in the resulting product for the purpose of determining the above-noted percentages.

In the nitrile reaction, as defined above, the primary reaction is a reaction which can be visualized as comprising the breaking of two existing unsaturated bonds between first and second carbon atoms and between third and fourth carbon atoms, respectively, and the formation of two new unsaturated bonds between said first and third and between said second and fourth carbon atoms. Said first and second carbon atoms and said third and fourth carbon atoms can be in the same or different molecules.

The nitrile reaction according to this invention is illustrated by the following reactions which are examples of the conversion of olefinically unsaturated nitriles:

(1) The disproportionation of an acyclic olefinically unsaturated nitrile having at least 3 carbon atoms into other olefinically unsaturated compounds of both higher and lower number of carbon atoms; for example, the disproportionation of propenenitrile yields ethylene and butenedinitrile; the disproportionation of 2,4-pentadienenitrile can yield a number of products such as ethylene, propenenitrile, 1,3-butadiene, 2,4,6-heptatrienenitrile and 2,4,6-octatrienedinitrile, 2,4,6-hexatriene, and butenedinitrile;

(2) The conversion of an acyclic mono- or polyene having three or more carbon atoms and a different acyclic mono- and polyene having three or more carbon atoms, at least one of said acyclic mono- or polyenes being a nitrile, to produce different acyclic unsaturated compounds; for example, the conversion of propylene and isobutenenitrile yields ethylene and 2-methyl-2-butenenitrile;

(3) The conversion of ethylene and an internal acyclic mono- or polyene nitrile having four or more carbon atoms to produce other unsaturated compounds having a lower number of carbon atoms than that of the acyclic mono- or polyene nitrile; for example, the conversion of ethylene and 4-methyl-2-pentenenitrile yields propenenitrile and 3-methyl-1-butene;

(4) The conversion of ethylene or an acyclic mono- or polyene having three or more carbon atoms and a cyclic mono- or cyclic polyene nitrile to produce an acyclic polyene nitrile having a higher number of carbon atoms than that of the starting nitrile; for example, the conversion of 4-cyanocyclooctene and 2-butene yields 5-cyano-2,10-dodecadiene;

(5) The conversion of one or more cyclic mono- or cyclic polyenes, at least one of the cyclic compounds being a nitrile, to produce a cyclic polyene nitrile having a higher number of carbon atoms than any of the starting materials; for example, the conversion of 3-cyclopentenecarbonitrile yields 1,6-cyclodecadiene-3,10-dicarbonitrile and continued reaction can give higher molecular weight material;

(6) The conversion of an acyclic polyene nitrile having at least eight carbon atoms and having at least five carbon atoms between any two double bonds to produce acyclic and cyclic mono- and polyenes having a lower number of carbon atoms than that of the feed; for example, the conversion of 2,7-octadienenitrile yields propenenitrile and cyclopentene;

(7) The conversion of one or more acyclic polyenes having at least three carbon atoms between any two double bonds, at least one of said polyenes being a nitrile, to produce acyclic and cyclic mono- and polyenes generally having both a higher and lower number of carbon atoms than that of the feed material; for example, the conversion of 2,5-hexadienenitrile yields 1,4-cyclohexadiene, ethylene, butenedinitrile, and propenenitrile.

The nitrile compounds which are applicable for use in the present invention are olefinically unsaturated and capable of being converted in the nitrile reaction. Among those suitable are those which are cyclic or acyclic, branched or unbranched, including aryl and cycloalkyl substituted olefinic nitriles, containing 3 up to about 20, preferably up to about 12 carbon atoms per molecule. These olefinic nitriles can contain up to about 5 cyano groups and can contain up to about 5 double bonds. However, mono- unsaturated mono- nitriles are presently preferred.

Some examples of nitrile compounds applicable for use in the invention are: propenenitrile (acrylonitrile), 2-butenenitrile, 3-butenenitrile, isobutenenitrile, 2-pentenenitrile, 3-pentenenitrile, 4-pentenenitrile, 2-methyl-3-butenenitrile, 2-methyl-3-ethyl-4-pentenenitrile, 3-cyclohexenecarbonitrile, 2,4-pentadienenitrile, 4-dodecenenitrile, 5-phenyl-3-pentenenitrile, 2-cyclopentyl-3-butenenitrile, 2-ethyl-4-decenedinitrile, 2,4,6,8,10-pentadecapentaene-1,4,6,9,12-pentacarbonitrile, 2-decyl-4-decenenitrile, and the like, and mixtures thereof.

The process can be carried out in the presence of non-nitrile olefin hydrocarbons. The olefin hydrocarbons which can be used as coreactants in the process of the present invention include cyclic and acyclic, branched or unbranched, mono- and polyolefins, including aryl and cycloalkyl substituted derivatives, containing 2 up to about 20, preferably up to about 12, carbon atoms per molecule. Ethylene can be used, in combination with internally unsaturated nitriles or cyclic unsaturated nitriles. The proportion of the olefin to unsaturated nitrile will, depending upon the nature of the reaction desired, usually vary within the range from about 1:10 to about 10:1. Where the desired reaction is primarily a reaction of a nitrile with an olefin hydrocarbon, the proportion will generally be about equimolar. Where both unsaturated nitriles and olefin hydrocarbons are present, the process is capable not only of converting the nitrile to other unsaturated nitriles but also converting the olefins to other olefins.

Some examples of applicable olefins are ethylene, propylene, butene-2,1,5-octadiene, 2-methylhexene-3, isobutene, 1-dodecene, 1,4-cyclohexadiene, allylbenzene, 4-cyclopentylpentene-1, 1,3,7-octatriene, heptene-2, 2,2-diethylnonene-4, 2,5,8,11,14-eicosapentaene, and the like, and mixtures thereof.

The catalysts which are applicable in the present invention include all of the solid catalysts which have activity for the disproportionation of propylene to ethylene and butene. Some examples of such catalysts are:

(1) Silica or thoria promoted by an oxide or a compound convertible to the oxide by calcination of tungsten, molybdenum, rhenium or tellurium or by a sulfide of tungsten or molybdenum. Included are catalysts comprising a silica-containing base wherein the amount of any alumina in said base is less than a preponderant amount;

(2) Alumina promoted with an oxide or compound convertible to an oxide by calcination of molybdenum, tungsten, or rhenium; a sulfide of tungsten or molybdenum; or an alkali metal salt, ammonium salt, alkaline earth metal salt, or bismuth salt of phosphomolybdic acid;

(3) One or more of the group aluminum phosphate, zirconium phosphate, calcium phosphate, magnesium phosphate, or titanium phosphate promoted by one or more of a sulfide of molybdenum or tungsten, or an oxide or a compound convertible to an oxide by calcination of molybdenum, tungsten, or rhenium or magnesium tungstate or beryllium phosphotungstate; and (4) Silica, alumina, aluminum phosphate, zirconium phosphate, calcium phosphate, magnesium phosphate, or titanium phosphate promoted by a hexacarbonyl of molybdenum or tungsten.

The catalysts of (1) can be prepared and activated by conventional techniques such as by combining a catalyst grade silica with suitable tungsten, molybdenum, rhenium or tellurium compounds by a conventional method such as, for example, impregnation, dry mixing, or coprecipitation. Suitable tungsten and molybdenum compounds include tungsten oxide and molybdenum oxide and compounds convertible to these oxides, tungsten sulfide and molybdenum sulfide. The supported oxides are activated by calcining in air and the supported sulfides are activated by heating in an inert atmosphere.

The catalyst of (2) can be prepared and activated by conventional techniques such as by combining catalyst grade alumina with an oxide or compound convertible to an oxide by calcination of molybdenum, tungsten or rhenium and calcining the resulting mixture after removal of any solvent used in the impregnation. The sulfides of tungsten or molybdenum or the salts of phosphomolybdic acid can be utilized to impregnate a catalyst grade alumina by solution in a proper solvent after which the solvent is evaporated and the resulting mixture dried to prepare the catalyst.

The catalyst compositions of (3) can be prepared and activated by conventional techniques. For example, molybdenum oxide can be coprecipitated with aluminum phosphate followed by calcination in air to produce an activated catalyst. Alternatively, the support material can be impregnated with a compound of the promoter convertible to the oxide, such as ammonium tungstate, followed by calcination in air. In the preparation of a sulfide-containing catalyst, a sulfide of the promoter can be ball milled with a support, such as zirconium phosphate, followed by heating in an inert atmosphere such as nitrogen. Magnesium tungstate and beryllium phosphotungstate can be dry mixed with titanium phosphate, for example, and activated by calcination in air at elevated temperatures.

The catalyst compositions of (4) can be prepared and activated by impregnating a previously calcined support material such as calcium phosphate with a solution of the hexacarbonyl of the promoter in an organic solvent such as benzene, followed by drying in a vacuum or in an inert atmosphere at about 50° to 700° F. (10° to 371° C.).

The catalytic agent is considered to be the reaction product resulting from the admixture of the support material and the promoter material and subsequent activation treatment.

The operating temperature for the process of this invention is generally in the range of about 0° to 1200° F. ($-18°$ to 649° C.). When using the catalysts of (1), it is in the range of about 400° to 1100° F. (204° to 573° C.); when using the catalysts of (2), in the range of about 150° to 500° F. (65° to 260° C.); when using the catalysts of (3), in the range of about 600° to 1200° F. (315° to 649° C.); when using the catalysts of (4), in the range of about 0° to 600° F. ($-18°$ to 315° C.) In the process of the invention, generally the pressure is not critical except with respect to the state of the materials in the reaction zone and with respect to conditions up and down stream from the reaction zone, but generally the pressure is in the range of 0 to 2000 psig.

The catalysts of the invention can be in the form of a powder, or granules, as well as in other shapes such as agglomerates, pellets, spheres, extrudates, beads, and other forms depending upon the type of contacting technique utilized.

With a fixed bed reactor and continuous operation, weight hourly space velocity in the range of 0.5 to 1000 parts by weight of hydrocarbon feed per part by weight of catalyst per hour (WHSV) are suitable, and excellent results have been obtained in the range of 1 to 200 WHSV.

Depending upon the specific feed materials and the specific catalyst being used, any conventional contacting technique can be utilized, such as fixed bed reaction, fluidized bed reaction, liquid phase batch reaction, and the like.

At the completion of the reaction, the reaction mixture can be processed to recover any desired product by any conventional means such as fractionation, crystallization, absorption, and the like. Unreacted materials or products not in the desired molecular weight range can be recycled.

The invention is further illustrated by the following examples:

EXAMPLE I

Conversion of Propenenitrile (Acrylonitrile) - Propylene Mixture

One part by volume of a WO₃/SiO₂ catalyst (containing about 7 weight percent WO₃) was charged to a fixed bed reactor and was activated in flowing air at 600° C. for 1 hour, flushed with nitrogen for 15 minutes, and cooled to 500° C. The fixed catalyst bed was then conditioned by a flow of propylene at 20 parts by volume propylene gas/min. for 1.5 hour while the reaction zone was maintained at about 500° C. and at atmospheric pressure. Propylene disproportionation products, namely ethylene and butenes, were obtained during this period.

A flow of propenenitrile was introduced at the rate of about 6.25 parts by volume propenenitrile gas/min. such that a mixture containing about 24 mol percent propenenitrile and about 76 mol percent propylene was passed into the reaction zone. The reactor effluent was sampled after 50 minutes and the reaction was allowed to continue for a total of 2 hours at 500° C.

The temperature of the reaction zone was then increased to 540° C. After 1 hour, the reaction effluent was sampled again.

Analysis of the reactor effluents showed that the conversion of propenenitrile to butenenitriles was 0.73 and about 2.0 percent at 500° C. and at 540° C. respectively. Ethylene and butenes also were produced.

The butenenitrile products were found to be a mixture of isomers as follows:

| Isomers | 500° C. | 540° C. |
|---|---|---|
| trans-Butenenitrile | 55.6 | 52.8 |
| cis₂-Butenenitrile | 37.4 | 38.4 |
| 3-Butenenitrile | 7.0 | 8.8 |

The data above show that a mixture of propylene and propenenitrile can be converted to butenenitriles by contact with an olefin disproportionation catalyst.

EXAMPLE II

Conversion of Propenenitrile (Acrylonitrile) Butene-2 Mixture

The same catalyst and apparatus as in Example I were used in this run. The catalyst was regenerated in flowing air at 500° C. for 1 hour and flushed with nitrogen for 15 minutes. The process of Example I then was repeated except that butene-2 was used in place of propylene. Butene-2 was passed through the reactor for 3 hours at 500° C. at atmospheric pressure and at 20 parts by volume/min. Propenenitrile was then added to the feed stream such that a mixture containing about 76 mol percent butene-2 and about 24 mol percent propenenitrile was passed through the reactor for about 30 minutes. The temperature was then raised to 550° C. and the effluent was sampled.

Analysis of the effluent showed that about 2 percent of the acrylonitrile was converted to butenenitriles. The butenenitrile product consisted of 51.7 weight percent trans-2-butenenitrile, 39.8 percent cis-2-butenenitrile, and 8.5 weight percent 3-butenenitrile.

These data show that propenenitrile can be converted to butenenitrile by contact with an olefin disproportionation catalyst when in admixture with either propylene or butene-2.

That which is claimed is:

1. A process for disproportionating propenenitrile with propylene to produce butenenitrile under disproportionation conditions with a catalyst comprising catalyst grade silica promoted with tungsten oxide wherein said disproportionation conditions include a temperature in the range of about 400° to 1100° F.

2. A process for disproportionating propenenitrile with butene-2 to produce butene-nitrile under disproportionation conditions with a catalyst comprising catalyst grade silica promoted with tungsten oxide wherein said disproportionation conditions include a temperature in the range of about 400° to 1100° F.

3. A process for disproportionating isobutene nitrile with propylene to produce ethylene and 2-methyl-2-butene nitrile under disproportionation conditions with a catalyst comprising catalyst grade silica promoted with tungsten oxide wherein said disproportionation conditions include a temperature in the range of about 400° to 1100° F.

4. A process for disproportionating isobutenenitrile with propylene to yield ethylene and 2-methyl-2-butenenitrile under disproportionation conditions with a catalyst selected from the group consisting of
    (1) silica or thoria promoted by an oxide of tungsten, molybdenum, rhenium or tellurium, or by a sulfide of tungsten or molybdenum;
    (2) alumina promoted with an oxide of molybdenum, tungsten or rhenium, a sulfide of tungsten or molybdenum, or with alkali metal salt, ammonium salt, alkaline earth metal salt, or bismuth salt of phosphomolybdic acid;
    (3) one or more of the group aluminum phosphate, zirconium phosphate, calcium phosphate, magnesium phosphate or titanium phosphate, promoted by one or more of a sulfide of molybdenum or tungsten, or by an oxide of molybdenum, tungsten or rhenium, or by magnesium tungstate or beryllium phosphotungstate; and
    (4) silica, alumina, aluminum phosphate, zirconium phosphate, calcium phosphate, magnesium phosphate or titanium phosphate promoted by a hexacarbonyl of molybdenum or tungsten;
    wherein said disproportionation is conducted at a temperature in the range of about 0° to 1200° F. with the proviso that when a catalyst of (1) is used the temperature is in the range of about 400° to 1100° F., when a catalyst of (2) is used the temperature is in the range of about 150° to 500° F., when a catalyst of (3) is used the temperature is in the range of about 600° to 1200° F., and when a catalyst of (4) is used the temperature is in the range of about 0° to 600° F.

5. A process for disproportionating 4-methyl-2-pentenenitrile with ethylene to yield propenenitrile and 3-methyl-1-butene under disproportionation conditions with a catalyst selected from the group consisting of
    (1) silica or thoria promoted by an oxide of tungsten, molybdenum, rhenium or tellurium, or by a sulfide of tungsten or molybdenum;
    (2) alumina promoted with an oxide of molybdenum, tungsten or rhenium, a sulfide of tungsten or molybdenum, or with an alkali metal salt, ammonium salt, alkaline earth metal salt, or bismuth salt of phosphomolybdic acid;
    (3) one or more of the group aluminum phosphate, zirconium phosphate, calcium phosphate, magnesium phosphate or titanium phosphate, promoted by one or more of a sulfide of molybdenum or tungsten, or by an oxide of molybdenum, tungsten or rhenium, or by magnesium tungstate or beryllium phosphotungstate; and (4) silica, alumina, aluminum phosphate, zirconium phosphate, calcium phosphate, magnesium phosphate or titanium phosphate promoted by a hexacarbonyl of molybdenum or tungsten;

wherein said disproportionation is conducted at a temperature in the range of about 0° to 1200° F. with the proviso that when a catalyst of (1) is used the temperature is in the range of about 400° to 1100° F., when a catalyst of (2) is used the temperature is in the range of about 150° to 500° F., when a catalyst of (3) is used the temperature is in the range of about 600° to 1200° F., and when a catalyst of (4) is used the temperature is in the range of about 0° to 600° F.

6. A process for disproportionating 4-cyanocyclooctene nitrile with 2-butene to yield 5-cyano-2,10-dodecadiene under disproportionation conditions with a catalyst selected from the group consisting of (1) silica or thoria promoted by an oxide of tungsten, molybdenum, rhenium or tellurium, or by a sulfide of tungsten or molybdenum;

(2) alumina promoted with an oxide of molybdenum, tungsten or rhenium, a sulfide of tungsten of molybdenum, or with an alkali metal salt, ammonium salt, alkaline earth metal salt, or bismuth salt of phsophomolybdic acid;

(3) one or more of the group aluminum phosphate, zirconium phosphate, calcium phosphate, magnesium phosphate or titanium phosphate, promoted by one or more of a sulfide of molybdenum or tungsten, or by an oxide of molybdenum, tungsten or rhenium, or by magnesium tungstate or beryllium phosphotungstate; and (4) silica, alumina, aluminum phosphate, zirconium phosphate, calcium phosphate, magnesium phosphate or titanium phosphate promoted by a hexacarbonyl of molybdenum or tungsten;

wherein said disproportionation is conducted at a temperature in the range of about 0° to 1200° F. with the proviso that when a catalyst of (1) is used the temperature is in the range of about 400° to 1100° F., when a catalyst of (2) is used the temperature is in the range of about 150° to 500° F., when a catalyst of (3) is used the temperature is in the range of about 600° to 1200° F., and when a catalyst of (4) is used the temperature is in the range of about 0° to 600° F.

7. A process for disproportionating propenenitrile with propylene to produce products comprising trans-2-butenenitrile cis-2-butenenitrile, 3-butenenitrile, ethylene, and butenes, under disproportionation conditions employing a catalyst which is tungsten oxide or silica, and wherein said disproportionation conditions include a contacting temperature in the range of about 400° to 1100° F., and a pressure in the range of about 0 to 2000 psig.

8. A process for disproportionating propenenitrile with butene-2 under disproportionation conditions to produce trans-2-butenenitrile, cis-2-butenenitrile, and 3-butenenitrile, under disproportionation conditions employing a catalyst which is tungsten oxide on a silica, and wherein said disproportionation conditions include a contacting temperature in the range of about 400° to 1100° F., and a pressure in the range of about 0 to 2000 psig.

9. The process according to claim 7 wherein the products of disproportionation are separated by an absorption process.

10. The process according to claim 7 wherein the products of said disproportionation are separated by fractional distillation.

11. The process according to claim 8 wherein the products of disproportionation are separated by an absorption process.

12. The process according to claim 8 wherein the products of said disproportionation are separated by fractional distillation.

13. The process according to claim 8 employing a propene nitrile: 2-butene admixture of about 24 mole percent propenenitirle:76 mole percent 2-butene.

14. The process according to claim 7 employing an admixture of about 24 mole percent propenenitrile:76 mole percent propylene.

* * * * *